United States Patent [19]

Toshihiko

[11] Patent Number: 4,541,059
[45] Date of Patent: Sep. 10, 1985

[54] STRESS DISTRIBUTION MEASURING INSTRUMENT

[75] Inventor: Fukuhara Toshihiko, Hadano, Japan

[73] Assignee: Kabushiki Kaisha Komatsu Seisakusho, Tokyo, Japan

[21] Appl. No.: 406,240

[22] PCT Filed: Dec. 4, 1981

[86] PCT No.: PCT/JP81/00365
§ 371 Date: Aug. 3, 1982
§ 102(e) Date: Aug. 3, 1982

[87] PCT Pub. No.: WO82/01939
PCT Pub. Date: Jun. 10, 1982

[30] Foreign Application Priority Data

Dec. 5, 1980 [JP] Japan ................. 55-170873

[51] Int. Cl.$^3$ ............................................. G01M 7/00
[52] U.S. Cl. ...................................... 364/508; 73/808; 374/47; 364/550
[58] Field of Search ............... 73/760, 763, 765, 808, 73/800, 813; 364/508, 550, 551, 571; 374/46, 47, 49, 51

[56] References Cited

U.S. PATENT DOCUMENTS 4,378,701 4/1983 Mountain et al. ............... 374/47 X

FOREIGN PATENT DOCUMENTS 52-78480 7/1977 Japan .

Primary Examiner—Edward J. Wise
Assistant Examiner—Edward R. Cosimano
Attorney, Agent, or Firm—Spensley Horn Jubas & Lubitz

[57] ABSTRACT

An external force is periodically applied to an object to be measured, a two-dimensional surface of the object is resolved and scanned by suitable infrared radiation detection means, and the infrared radiation at the times of maximum and minimum loading by the external force are detected for the respective resolved zones. The difference between the infrared radiation at the maximum and the minimum loading times is then calculated for every resolved zone. Further, the calculated values are multiplied by correction values corresponding to the shape, material, infrared radiation rate and so forth of the object. The thus obtained values are suitably visibly indicated in the positions of the respective zones. This indication is ordered by suitably slicing the levels of the thus obtained values to identify and display them in accordance with an ordering scheme.

6 Claims, 5 Drawing Figures

STRESS DISTRIBUTION MEASURING INSTRUMENT

TECHNICAL FIELD

This invention relates to a stress distribution measuring instrument for measuring a stress distribution of a welded structure, a machine component, etc.

BACKGROUND ART

In order to design and fabricate a welded structure, a machine component, etc. with a good balance of strength and weight in the structure, it is generally useful to know the stress distribution of these objects when a force is applied thereto.

Conventional stress distribution measuring instruments employing a photo-elastic method and employing a stress coating method are heretofore known. However, all of these instruments have disadvantages in that a thin uniform membrane of several hundred microns should be attached to the surface of the object to be measured, and therefore have difficulties in measuring the stress distribution of a large-sized structure. This is true particularly in the stress coating method, since measurement in such a method utilizes the brittleness of an organic substance and controlling the dry condition of the membrane attached to the object to be measured is very difficult. Further, the membrane itself has an unfavorable toxicity.

Thus, conventional stress distribution measuring causes a variety of inconveniences in actual use and is particularly unsuitable for the measurement of the stress distribution of large objects and actual mechanical apparatus, etc.

Accordingly, an object of this invention is to provide a stress distribution measuring instrument in which all of the above-described difficulties accompanying conventional methods have been eliminated, and in which the stress distribution of an object to be measured can be accurately measured without conducting any processing such as attaching any membrane, etc. to the object. Hence, accurate measurement can be performed irrespective of the configuration and the size of the object to be measured.

DISCLOSURE OF THE INVENTION

The invention utilizes the fact that, when an external force, e.g., adiabatic compression or expansion, is applied to a solid, a variation in the quantity of heat occurs in proportion to the amplitude of the strain of the solid as in the case of a gas or liquid. In accordance with this invention, a desired stress distribution is obtained by applying an external force periodically to the solid or object to be measured, using an adaquate scanning means together with an infrared radiation detection means to detect the quantity of irradiated infrared rays for various zones along the two-dimensional plane of the object at the maximum and minimum loading time of the external force, storing the quantities, calculating the difference between the quantities of the infrared radiation at the maximum loading time and at the minimum loading time at every zone with calculating means, and visually displaying the calculated value at the corresponding locations to the respective zones. It is preferred to correct the above calculation in accordance with parameters such as the shape, material, and infrared radiation rate of the object to be measured when carrying out the calculation.

In the stress distribution measuring instrument according to this invention, the distribution of the infrared radiation quantity occuring on the surface of the object to which an adequate external force is applied is detected and analyzed, whereby the stress distribution in the object can be measured without applying any processing to the object. Further, since it is not necessary to conduct any processing on the object at all, measurement of the stress distribution can be effectively and accurately performed regardless of shape and size of the object.

BEST MODE OF CARRYING OUT THE INVENTION

A principle of the present invention will now be described for ready understanding of the invention.

When the relationship between the strain and the change in temperature of a solid is considered, irradiation or absorption of infrared rays proportional to the quantity of strain will occur at the solid in the same manner as a gas or liquid when an external force such as adiabatic compression or expansion is applied. Thus, it is understood that the following relation is derived from the above fact;

(Quantity of strain)α(Quantity of variation in temperature).

Since the following equation holds for the stress $\sigma$ $$\sigma = E\epsilon$$

where $\epsilon$ represents the quantity of strain and E represents Young's modulus, the stress in this solid can be obtained if the variation in the temperature in proportion to the quantity of the strain is obtained.

Now the relationship between the changes in temperature and the quantity of infrared radiation will be considered. Then, the quantity IR of the infrared radiation becomes:

$$IR = T^4 K \text{ (Kirchhoff's law)}$$

where T (absolute temperature) represents the change in temperature, and K represents the infrared radiation rate (a value determined by a substance and the surface state thereof), and it is also understood from the above that there is a proportional relationship between the quantity of infrared radiation and the change in temperature.

Figure 1:
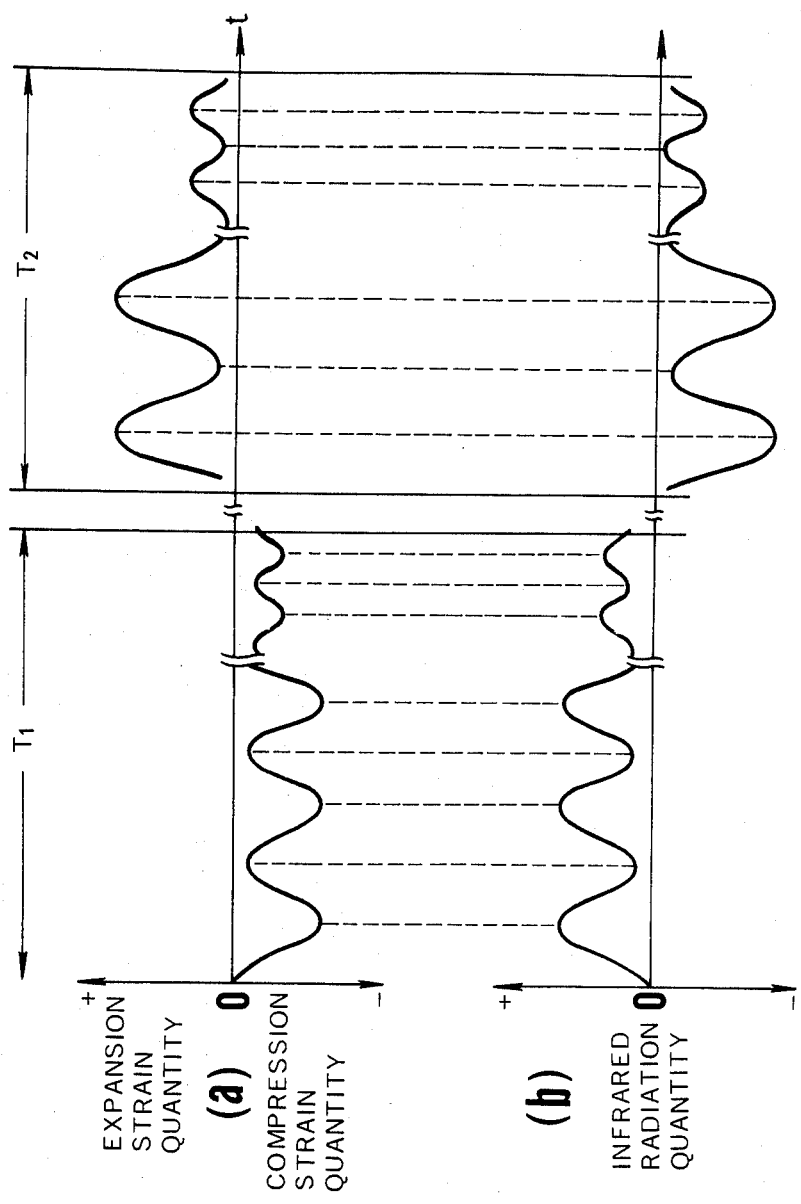
FIG. 1 is a graphical diagram showing the relationship between the quantity of strain and the quantity of infrared radiation.

Accordingly, in order to learn the stress in a solid, it is only necessary to measure the quantity of the infrared radiation irradiated when a compression or expansion strain occurs in the solid as a result of the external force applied thereto. FIG. 1 shows the relationship between the quantity of strain and the quantity of infrared radiation.

Referring to FIG. 1 (a) represents the quantity of the strain in a solid, and (b) represents the quantity of infrared radiation irradiated from the solid. It is understood from FIG. 1 that irradiation of infrared rays (exotherm) in a quantity proportional to the quantity of the strain occurs during the period $T_1$ in which a compression strain takes place by the external force applied to the solid; absorption of the infrared rays (endotherm) proportional to the quantity of the strain occurs during the period $T_2$ in which an expansion strain takes place at the solid.

In the case of a solid, when an external force is applied, a stress distribution specific to its condition based on its shape, quantity, etc. will occur at the solid, and irradiation or absorption of a great deal of infrared rays occurs at the portion in which large strain takes place and irradiation or absorption of the infrared rays of small quantity will occur at the portion in which small strain takes place.

Therefore, the stress distribution in an object to be measured, such as a welded structure or machine component, can be determined by measuring the distribution of the quantity of infrared radiation emitted when an external force is applied to the object and compression or expansion strain is caused to occur at the object.

The stress distribution measuring instrument according to this invention will now be described in detail with reference to the preferred embodiment shown in FIG. 2.

Figure 2:
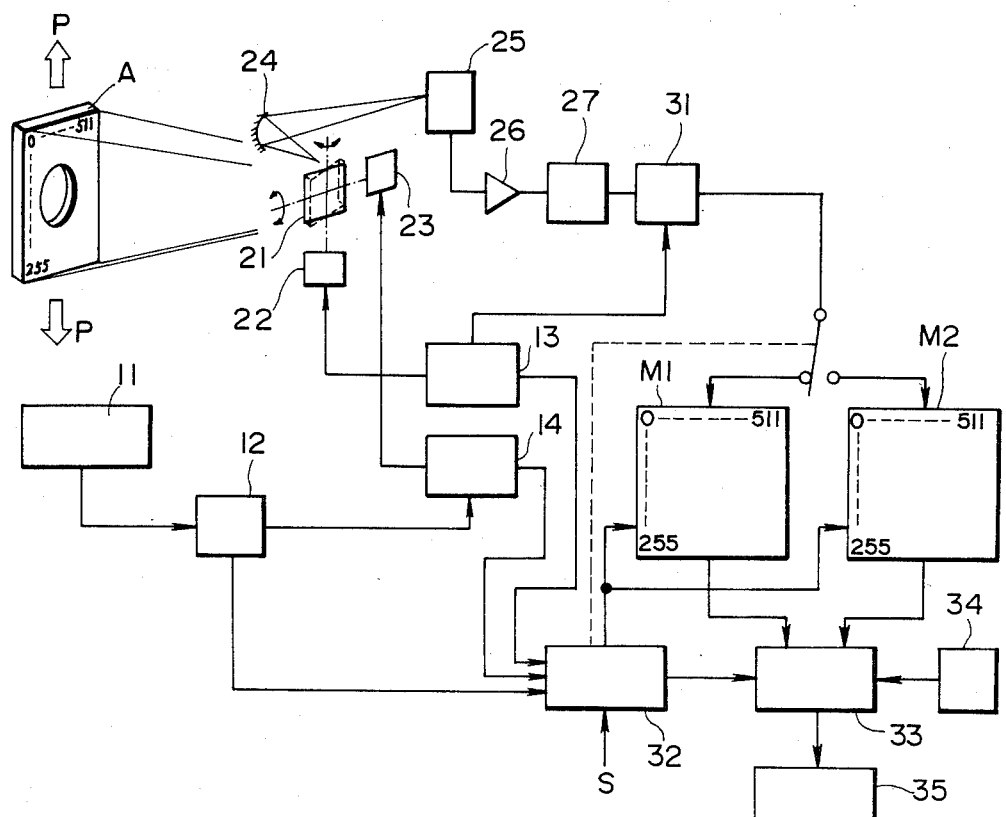
FIG. 2 is a block diagram showing one preferred embodiment of the stress distribution measuring instrument according to the present invention.
Figure 3:
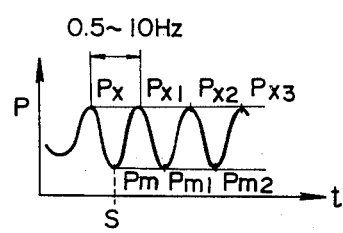
FIG. 3 is a graphical diagram showing the state of the external force applied to the object to be measured.

In FIG. 2, reference character A represents an object to be measured, to which an external force P is applied by an adequate loading device (not shown). When a strain distribution occurs at the object A, the infrared radiation whose distribution corresponds to the strain distribution will be generated. In FIG. 3, the above external force P is applied at a predetermined frequency (0.5 Hz to 10 Hz) and a predetermined amplitude as shown in FIG. 3, and the quantity distribution of the infrared radiation will vary in accordance with the frequency and the amplitude of the external force P.

The stress distribution measuring instrument of the preferred embodiment generally comprises: a camera controlling section having an external force detector 11, a phase synchronizer 12, a horizontal scan oscillator 13 and a vertical scan oscillator 14; an infrared radiation camera having a scanning mirror 21, a rocking device 22, a step motor 23, a concave mirror 24, an infrared radiation detector 25, a preamplifier 26 and a linearizer 27; and a data processor having memories M1 and M2, an A/D converter 31, processors 32 and 33, a parameter setting unit 34, a ranking unit 35 and a display unit 36. The functions and the operations of the respective sections, devices and units will be described in detail.

The external force detector 11 mounted on the loading device or in other places serves to detect the maximum and minimum loading times at each period during which the external force P (Refer to FIG. 3) is applied as well as the duration of the period, and the detection signal from the external force detector 11 is in turn applied to the phase synchronizer 12.

The phase synchronizer 12 serves to control the oscillation frequency of the vertical scan oscillator 14 in accordance with the detection signal from the external force detector 11 and so operates as to synchronize the oscillation frequency with the frequency of the applied external force P. This phase synchronizer 12 also supplies information on the maximum and minimum loading times sequentially detected by the external force detector 11 into the first processor 32.

The vertical scan oscillator 14 serves to supply a signal whose frequencies are controlled by the phase synchronizer 12 into the step motor 23. In this manner, the step motor 23 tilts the scanning mirror 21 at a rate of one step at every one period of the applied external force with respect to the Y-axis (vertical) direction. The oscillation signal from the vertical scan oscillator 14 is also applied to the first processor 32 and is used as one synchronizing signal when carrying out data processing described later.

The horizontal scan oscillator 13 serves to supply the rocking device 22 with a signal whose frequency is sufficiently higher (e.g., higher by 10 or 100 times) than the oscillation frequency at the vertical scan oscillator 14 so as to continuously drive the rocking device 22. In this manner, the rocking device 22 serves to rock the scanning mirror 21 in the X-axis (horizontal) direction at high speed. Further, the oscillation signal from the horizontal scan oscillator 13 is also applied to the A/D converter 31 and the first processor 32, and is used as one of the synchronizing signals when carrying out the data processing, which will be described later.

The scanning mirror 21 serves to sequentially scan over the two-dimensional plane of the object A by the high speed rocking in the X-axis direction and by the stepwise tilting with respect to the Y-axis direction so as to decompose and reflect the infrared rays emitted from the two-dimensional surface of the object at every interval onto the concave mirror 24, which are then received by the infrared radiation detector 25.

The infrared radiation detector 25 serves to output an electrical signal corresponding to the quantity of the infrared radiation detected to the linearizer 27 through the preamplifier 26 for linearization of the signal.

The A/D converter 31 serves to conduct sampling on the output analog signal (infrared radiation quantity data) from the linearizer 27 in accordance with the oscillation signal period of the horizontal scan oscillator 13 in order to convert the sampled signal into digital signals responsive to the levels of the signals. The infrared radiation quantity data thus converted into digital form is written or loaded into the memory M1 or M2 under the control of the first processor 32 and is then read therefrom. More particularly, the first processor 32 serves to form a predetermined address signal in accordance with the period of the oscillation signal of the horizontal and vertical scan oscillators 13 and 14 and to control the loading of the infrared radiation quantity data at the desired time point selectively into the memory M1 or M2. When the start signal S is applied the aforementioned series of steps are started. The first processor 32 also serves to form similarly the predetermined address signal when the date loaded in the memories M1 and M2 are read and to control the reading of the predetermined data sequentially. In reading, two data words in the memories M1 and M2 having the same address are simultaneously read. In this embodiment, 128k word memory having 512 X addresses (addresses 0 to 511) and 256 Y addresses (addresses 0 to 255) is used as the memories M1 and M2 as shown in FIG. 2.

The second processor 33 serves to calculate the difference between the two data words sequentially read by the first processor 32, and to calculate and correct the calculated values, in accordance with parameters such as shape, material, infrared radiation rate, etc. of the object A supplied from the parameter setting unit 34. The data thus corrected and calculated are sequentially applied to the ranking unit 35.

The ranking unit 35 serves to place a rank or order on the data thus received from the second processor 33 in accordance with the magnitude of the date into, for example, 10 to 25 grades.

The display unit 36 serves to suitably classify (e.g., the color classification) the respective data ranked into 10 to 15 grades corresponding to the ranking and to reproduce and display the classified data corresponding to positions where the data have been collected from the object A.

Figure 4:
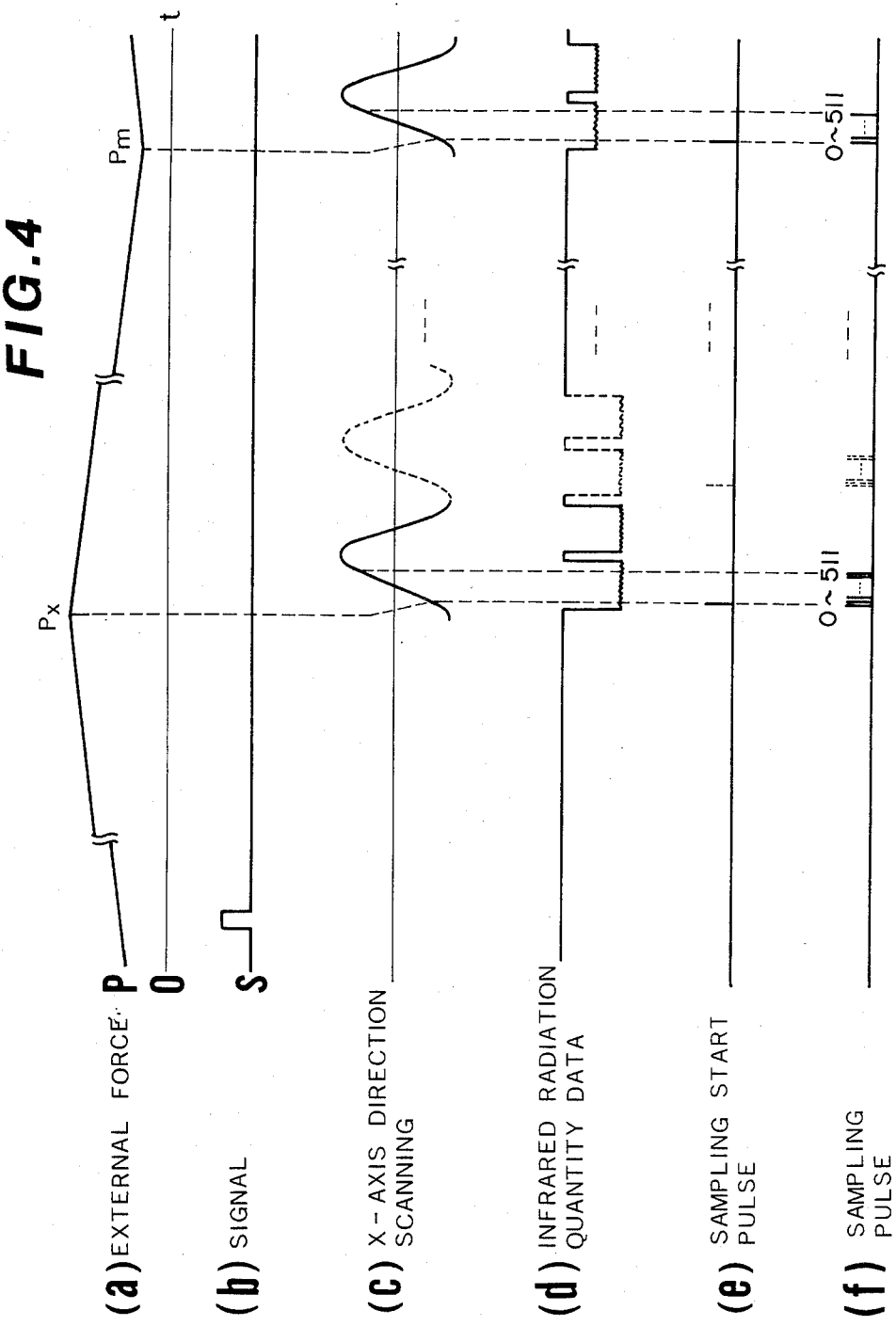
FIG. 4 is a timing chart showing a part of the operation of the above embodiment.

The operation of the infrared radiation measuring instrument of this embodiment will now be described. FIG. 4 illustrates a timing chart showing the timing at which the infrared radiation quantity data are obtained.

When the start signal S is inputted into the first processor 32 at the timing shown in FIG. 4(b), the first processor 32 selectively connects the memory M1 to the A/D converter 31 at the time when the first maximum loading time $P_{x1}$ of the external force P is detected by the external force detector 11 (FIG. 4(a)). At this time the scanning mirror 21 scans in the X-axis direction with respect to the position of "0" in the Y-axis direction on the two-dimensional surface of the object A (Refer to FIG. 4(c).), and the infrared radiation quantity data corresponding to the scanning (Refer to FIG. 4(d).) is applied through the infrared radiation detector 25, the preamplifier 26 and the linearizer 27 to the A/D converter 31. Then, the A/D converter 31 conducts sampling on the infrared radiation quantity data of one scan of the scanning mirror 21 for data point corresponding to the number of X addresses of the memories M1 and M2. That is, the A/D converter samples 512 times in response to the sampling start pulse (Refer to FIG. 4(e).) produced in synchronization with the oscillation signal from the horizontal scan oscillator 13, and then digitally converts the sampled signal. In the meantime, the first procesor 32 designates the writing address to the memory M1 in synchronization with the sampling in the A/D converter 31, and the infrared radiation quantity data thus digitally converted is loaded at the respective words of the memory M1 with address of "0" and X addresses of "0" to "511" (Refer to FIG. 4(f).

Then, when the first minimum loading time $P_{m1}$ of the external force P shown in FIG. 4(a) is detected by the external force detector 11, the first processor 32 selects and connects the memory M2 to the A/D converter 31. Accordingly, the infrared radiation quantity data thus corresponding to the scanning at this time are digitally converted and are loaded in the respective words of the memory M2 with Y address "0" and X addresses of "0" to "511".

Thus, the infrared radiation quantity data at the maximum loading time of the external force are loaded in the memory M1, and the infrared radiation quantity data at the minimum loading time of the external force are loaded in the memory M2.

When the aforementioned operation has completed, the vertical scan oscillator 14 dispatches a signal to the step motor 23 to came a sweep movement of the scanning mirror 21 in the amount of 1/256 of the deflecting angle with respect to the Y-axis direction. Simultaneously, it also dispatches a signal to the first processor 32 whereby the Y-axis input word position of the memories M1 and M2 is advanced from "0" to "1".

Thereafter, the Y address of the memory M1 is similarly loaded with the infrared radiation quantity data at the maximum loading time in memory locations with a Y address of "1" and X addresses of "0" to "511", and the infrared radiation quantity data at the minimum loading time are loaded in memory locations with a Y address of "1" and of X addresses of "0" to "511" of the memory M2.

When the above-described operation is repeated and the measurments corresponding to a Y-address of "255" are completed, the first processor 32 sequentially reads the infrared radiation quantity data loaded in the words of the memories M1 and M2 whose addresses are the same and applies these data to the second processor 33. The second processor 33 calculates, for example, the difference represented by the following formula:

(Infrared radiation quantity at minimum loading time)−(Infrared radiation quantity at maximum loading time)

and then multiplies it by the parameter supplied by the parameter setting unit 34 to carry out the suitable data correction. If the difference is positive, it means the occurrence of the expansion strain, and if it is negative, it means the occurrence of the compression strain at the object. The calculated data thus obtained are suitably ranked as described above, and are visually displayed as a stress distribution diagram.

Figure 5:
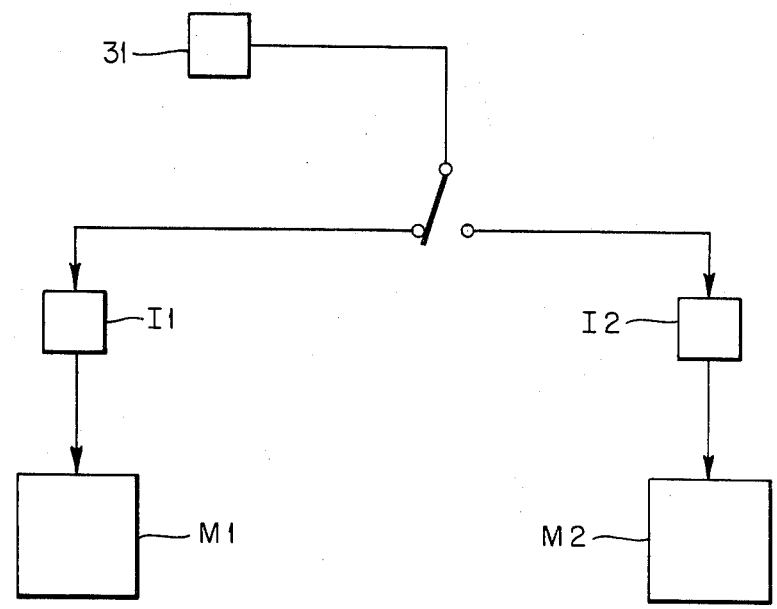
FIG. 5 is a block diagram showing the use of integrators.

In this embodiment, the S/N (signal/noise) ratio can be improved when suitable integrators I1 and I2, as shown in FIG. 5, are interposed at the inputs of the memories M1 and M2, and the data loaded into the memories are integrated at prescribed times. That is, the exotherm or endotherm caused by the external force can be retained for a short time, and the temperature sensitivity of the apparatus can be improved, thus improving the resolution capacity when scanning operations are repeated in the meantime and the infrared radiation quantity data thus obtained at the respective scannings are integrated.

Though the foregoing description in this embodiment is directed to the application of an external force by an adequate loading device to the object A to be measured, the stress distribution can be measured in the actual load state depending upon the object to be measured. For instance, in the case where the object is the hull of a ship and it is actually floated on the sea, the external force utilized is the pressure of the waves applied periodically to the hull of the ship.

Further, the scanning method of the two-dimensional surface of the object as exemplified in this invention can be any type. Any method may be employed if the infrared radiation quantity data at the maximum and minimum loading times can be collected from all the zones of the two-dimensional surface of the object in the scanning. If the stress distribution of a part of the object to be measured is desired, that part of the object may be selectively scanned and the infrared radiation quantity data at the part of the object may be collected.

In the above-described embodiment, the data collected with the memories M1 and M2 are temporarily stored. However, it may be so constructed as to display the stress distribution in real-time simultaneously upon collection of the data. It may also be so constructed as to suitably store the raw data collected at the measuring field in the PCM modulated manner, and to process the stored data in offline. In this case, the oscillation frequency of the horizontal scan oscillator 22 is set at 60 Hz, and the above data are conveniently synchronized with the vertical period of a TV for reproducing and displaying the data.

INDUSTRIAL APPLICABILITY

In the foregoing description, the stress distribution measuring instrument according to this invention is very simple to use and can measure effectively and accurately the stress distribution of an object to be measured regardless of the shape and size. In particular, this invention can advantageously perform the stress distribution measurements of objects such as a chassis of a vehicle, iron bridges, the hull of a ship, and subassemblies of various construction machines.

I claim:

1. A stress distribution measuring instrument comprising:
   infrared radiation detection means for resolving and scanning the surface of an object to be measured to which a periodically varying load is applied and for separately detecting and outputting the quantities of infrared radiation at the maximum and minimum loading times respectively at respective resolved zones of said surface,
   calculating means for calculating the difference between the detected quantity of infrared radiation at the maximum loading time and the detected quantity of infrared radiation at the minimum loading time at every resolved zone, and,
   display means for visually displaying the values calculated by said calculating means corresponding to the location of the respective resolved zone.

2. The stress distribution measuring instrument as claimed in claim 1 wherein said infrared radiation detection means comprises first and second memories for storing respectively the quantities of infrared radiation detected at the maximum and minimum loading times at every resolved zone.

3. The stress distribution measuring instrument as claimed in claim 2 wherein said infrared radiation detection means further comprises:
   integrators at the inputs of said first and second memories, respectively, said detection means detecting the quantities of infrared radiation at the maximum and minimum loading times at every resolved zone a plurality of times, said integrators integrating said quantities detected respectively for said maximum and minimum loading times said plurality of times, the resultant integrated values of quantities of infrared radiation being stored respectively in said first and second memories.

4. The stress distribution measuring instrument as claimed in claim 1 wherein said display means ranks the calculated values within a predetermined number of levels, and identifies and displays the values corresponding to the ranking.

5. A stress distribution measuring instrument according to claim 1 further comprising:
   means for producing signals indicating minimum and maximum loading times and for causing infrared radiation detection means to detect said quantities of radiation separately and independently in response to said respective minimum and maximum loading time indicating signals.

6. A stress distribution measuring instrument according to claim 1 further comprising:
   A/D converter means for converting said detected quantities of infrared radiation to digital values and wherein said calculating means operates digitally on said digital values.

* * * * *